United States Patent
Chen et al.

(10) Patent No.: US 10,488,381 B2
(45) Date of Patent: Nov. 26, 2019

(54) TEMPERATURE AND HUMIDITY SENSING DEVICE

(71) Applicants: Yu-Ju Chen, Taipei (TW); Hsiu-Chin Yeh, Taipei (TW); Yen-Lin Chen, Taipei (TW); Min-Hsiung Lin, Taipei (TW)

(72) Inventors: Yu-Ju Chen, Taipei (TW); Hsiu-Chin Yeh, Taipei (TW); Yen-Lin Chen, Taipei (TW); Min-Hsiung Lin, Taipei (TW)

(73) Assignee: COMPAL ELECTRONICS, INC., Taipei (TW)

(*) Notice: Subject to any disclaimer, the term of this patent is extended or adjusted under 35 U.S.C. 154(b) by 152 days.

(21) Appl. No.: 15/693,480

(22) Filed: Sep. 1, 2017

(65) Prior Publication Data

US 2018/0067093 A1  Mar. 8, 2018

Related U.S. Application Data

(60) Provisional application No. 62/384,181, filed on Sep. 6, 2016.

(51) Int. Cl.
*G01N 33/00* (2006.01)
*G01K 1/08* (2006.01)
(Continued)

(52) U.S. Cl.
CPC .......... *G01N 33/0062* (2013.01); *G01K 1/08* (2013.01); *G01K 13/02* (2013.01);
(Continued)

(58) Field of Classification Search
None
See application file for complete search history.

(56) References Cited

U.S. PATENT DOCUMENTS 6,347,746 B1 * 2/2002 Dage .................. B60H 1/00785
236/44 C
8,570,175 B2  10/2013 Rahimi
(Continued)

FOREIGN PATENT DOCUMENTS

| CN | 204521231 | 8/2015 |
| TW | I481866 | 4/2015 |
| TW | M511841 | 11/2015 |

OTHER PUBLICATIONS

"Office Action of Taiwan Counterpart Application", dated Apr. 9, 2018, p. 1-p. 6, in which the listed reference was cited.

*Primary Examiner* — Andre J Allen
(74) *Attorney, Agent, or Firm* — JCIPRNET

(57) ABSTRACT

A temperature and humidity sensing device including a body and a temperature and humidity sensor is provided. The body has an inlet hole, an outlet hole, and a flow channel. The inlet hole and the outlet hole are opposite to each other, and the flow channel is configured to communicate the inlet hole and the outlet hole. The temperature and humidity sensor is disposed in the flow channel. The temperature and humidity sensor is configured to sense the relative humidity of air in the surrounding environment of the body during the air in the surrounding environment of the body flows into the flow channel from the inlet hole and flows through the flow channel to flow out from the outlet hole.

10 Claims, 5 Drawing Sheets

(51) Int. Cl.
*G01K 13/02* (2006.01)
*G01N 1/22* (2006.01)
(52) U.S. Cl.
CPC ... *G01N 33/0036* (2013.01); *G01K 2013/024* (2013.01); *G01N 2001/2276* (2013.01)

(56) References Cited

U.S. PATENT DOCUMENTS

| | | | | |
|---|---|---|---|---|
| 2016/0161313 A1* | 6/2016 | Yamaguchi | ............ | G01F 1/684 73/114.34 |
| 2016/0162256 A1* | 6/2016 | Komaromi | ............... | A61B 5/01 700/94 |
| 2017/0059381 A1* | 3/2017 | Ban | ......................... | G01F 1/696 |

* cited by examiner

TEMPERATURE AND HUMIDITY SENSING DEVICE

CROSS-REFERENCE TO RELATED APPLICATION

This application claims the priority benefit of U.S. provisional application Ser. No. 62/384,181, filed on Sep. 6, 2016. The entirety of the above-mentioned patent application is hereby incorporated by reference herein and made a part of this specification.

BACKGROUND OF THE INVENTION

Field of the Invention

The invention relates to a sensing device, and more particularly, to a temperature and humidity sensing device.

Description of Related Art

In the common temperature and humidity sensing device, a temperature and humidity sensor is generally disposed in the case, and a single opening is left on the case to allow air in the surrounding environment of the temperature and humidity sensing device to flow into the case from the opening, such that the relative humidity of the air in the surrounding environment of the temperature and humidity sensing device is obtained via the temperature and humidity sensor disposed in the case. However, the temperature and humidity sensing device having a single opening design has drawbacks such as worse sensing efficiency and worse sensing accuracy.

SUMMARY OF THE INVENTION

The invention provides a temperature and humidity sensing device that can increase sensing efficiency and sensing accuracy.

The temperature and humidity sensing device of the invention includes a body and a temperature and humidity sensor. The body has an inlet hole, an outlet hole, and a flow channel. The inlet hole and the outlet hole are opposite to each other, and the flow channel is configured to communicate the inlet hole and the outlet hole. The temperature and humidity sensor is disposed in the flow channel. The temperature and humidity sensor is configured to sense the relative humidity of air in the surrounding environment of the body during the air in the surrounding environment of the body flows into the flow channel from the inlet hole and flows through the flow channel to flow out from the outlet hole.

In an embodiment of the invention, the body includes a first case and a second case connected to each other, the inlet hole is disposed on the first case, and the outlet hole is disposed on the second case.

In an embodiment of the invention, the inside of the first case has a groove and a trench. The groove is communicated with the inlet hole and the groove is communicated with the trench. The temperature and humidity sensor is located in the groove.

In an embodiment of the invention, the temperature and humidity sensing device further includes a diversion tube disposed between the first case and the second case. The diversion tube is configured to communicate the trench and the outlet hole and the flow channel is formed by the groove, the trench, and the diversion tube.

In an embodiment of the invention, the temperature and humidity sensing device further includes a circuit board disposed between the first case and the second case and covering the groove. The temperature and humidity sensor is disposed at a side of the circuit board covering the groove and electrically connected to the circuit board.

In an embodiment of the invention, the temperature and humidity sensing device further includes a gasket disposed on the first case and located between the circuit board and the first case. The gasket covers a portion of the trench and has a first opening and a second opening opposite to each other. The first opening is aligned to the groove and the second opening is aligned to the diversion tube. The circuit board covers the first opening and the temperature and humidity sensor passes through the first opening.

In an embodiment of the invention, the gasket is located between the diversion tube and the first case, and the second opening exposes a portion of the trench such that the trench and the diversion tube are communicated with each other.

In an embodiment of the invention, the diversion tube has an inlet port, an outlet port opposite to the inlet port, and a conduit, wherein the inlet port is communicated with the trench, the conduit communicates the inlet port and the outlet port, and the outlet port is communicated with the outlet hole.

In an embodiment of the invention, the diameter of the conduit is constant.

In an embodiment of the invention, diameter of the conduit is increased from the inlet port toward the outlet port.

In an embodiment of the invention, the temperature and humidity sensing device further includes a gasket disposed between the diversion tube and the second case. The gasket has an opening configured to communicate the diversion tube and the outlet hole.

Based on the above, the temperature and humidity sensing device of the invention has an inlet hole and an outlet hole at two opposite sides of the body such that air in the surrounding environment of the body can flow into the flow channel from the inlet hole and flow out of the flow channel from the outlet hole. As a result, unidirectional air flows through the temperature and humidity sensor disposed in the flow channel, such that the sensing efficiency and the sensing accuracy of the temperature and humidity sensor can be increased.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
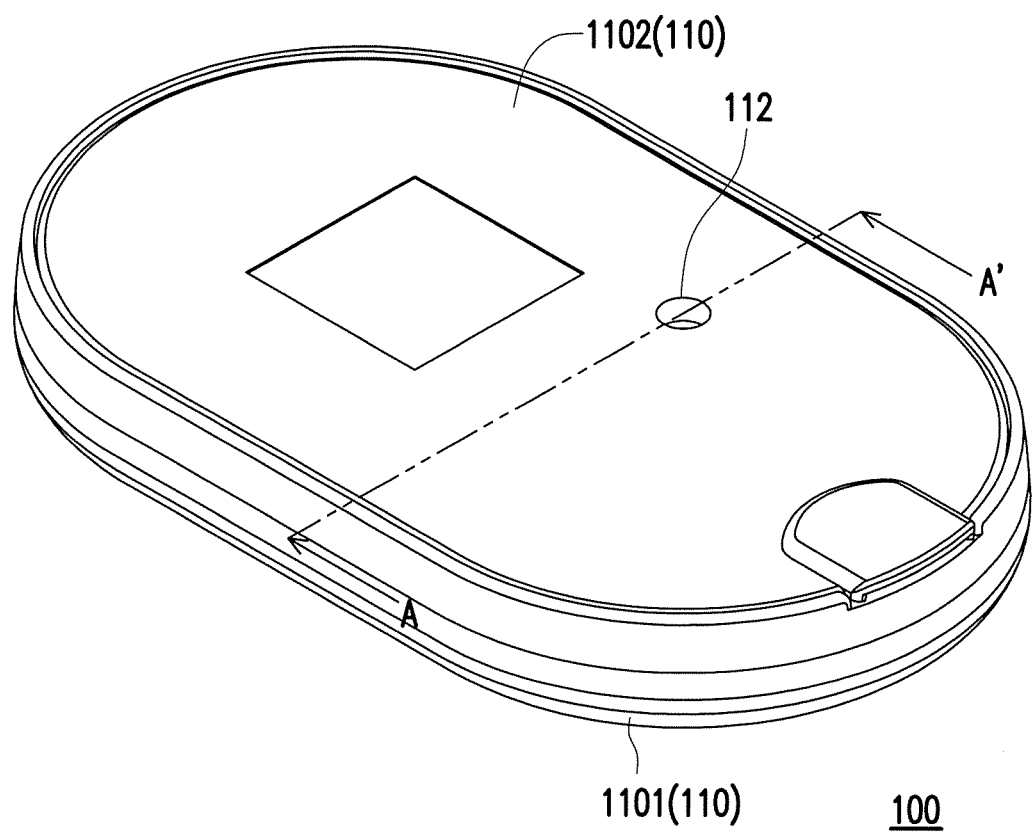
FIG. 1 is a schematic of a temperature and humidity sensing device of an embodiment of the invention.
Figure 2:
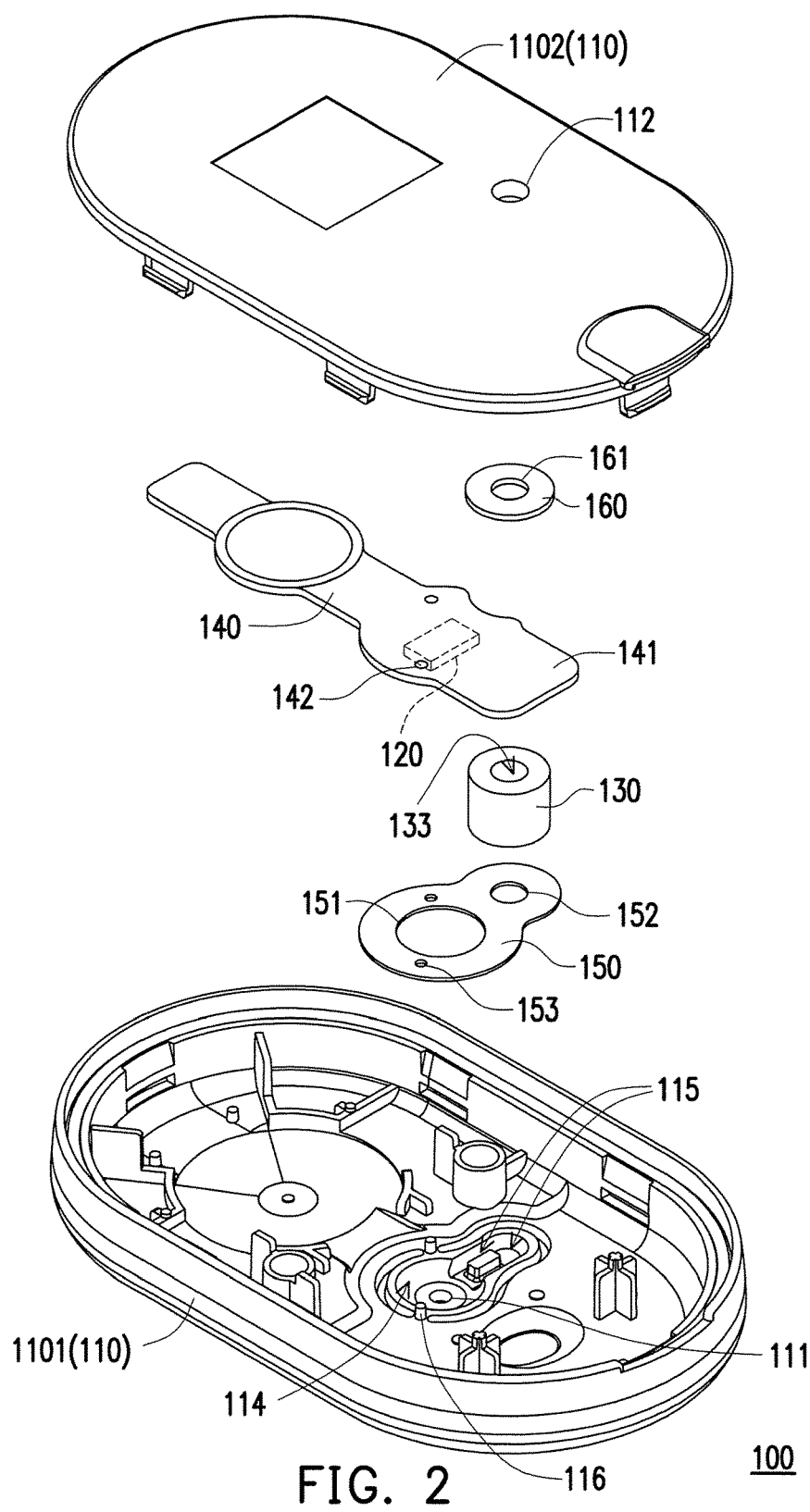
FIG. 2 is an exploded view of the temperature and humidity sensing device of FIG. 1.
Figure 3:
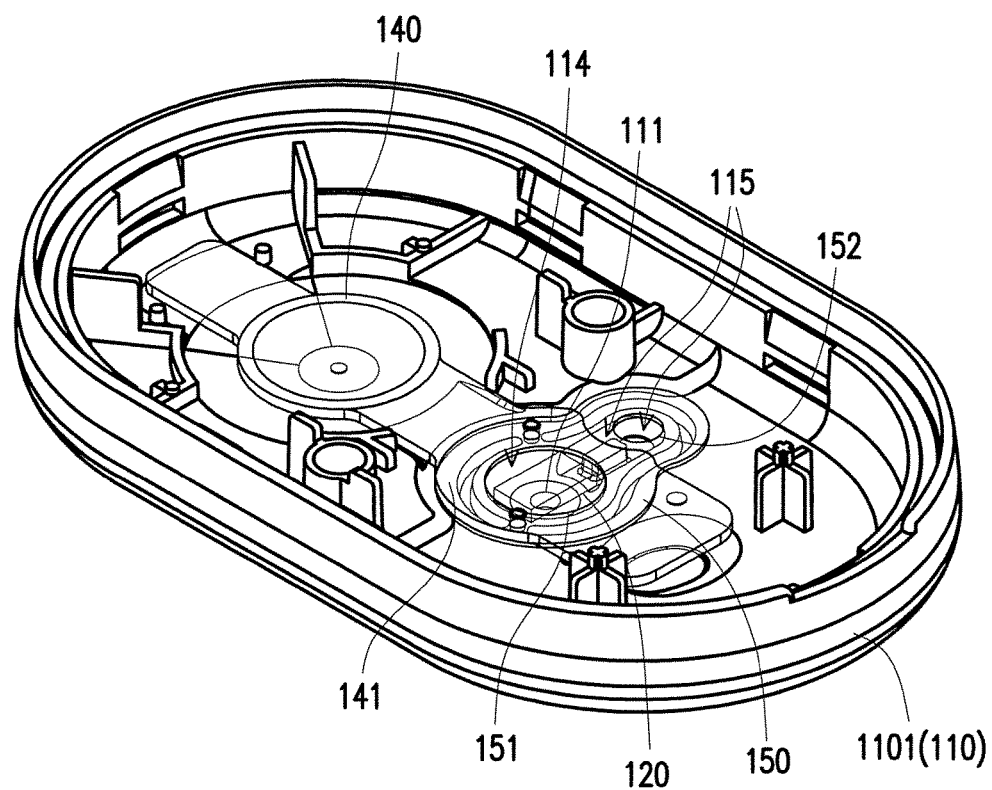
FIG. 3 is a structure configuration diagram of the first case, the gasket, the circuit board, and the temperature and humidity sensor of FIG. 2.
Figure 4:
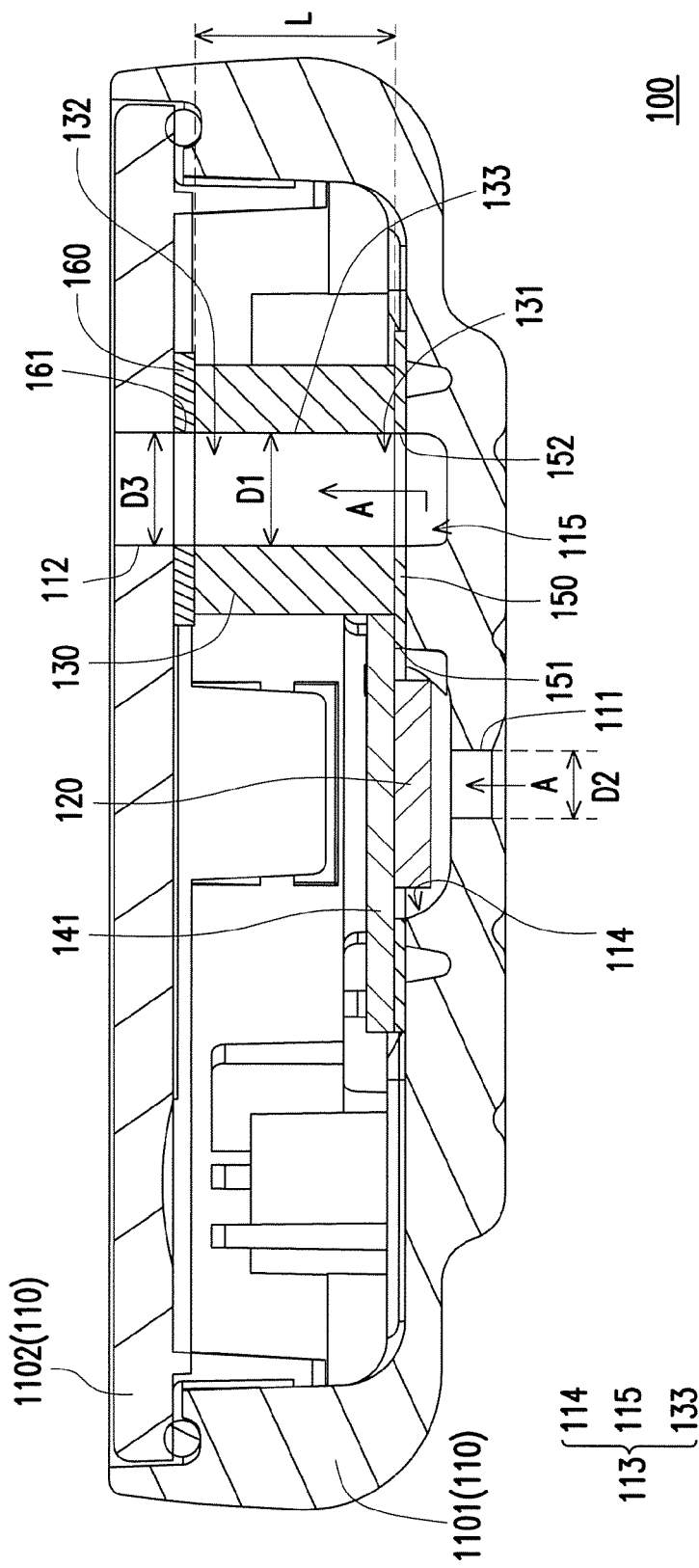
FIG. 4 is a cross section of the temperature and humidity sensing device of FIG. 1 along section line A-A'.

FIG. 1 is a schematic of a temperature and humidity sensing device of an embodiment of the invention. FIG. 2 is an exploded view of the temperature and humidity sensing device of FIG. 1. FIG. 3 is a structure configuration diagram of the first case, the gasket, the circuit board, and the temperature and humidity sensor of FIG. 2. FIG. 4 is a cross section of the temperature and humidity sensing device of FIG. 1 along section line A-A'. For clarity and ease of illustration, a circuit board 140, a gasket 150, and a temperature and humidity sensor 120 of FIG. 3 are shown in a perspective manner. Referring to FIG. 1 to FIG. 4, in the present embodiment, the temperature and humidity sensing device 100 can be configured to sense the relative humidity in a diaper, the relative humidity of other objects worn on the human body, or the relative humidity of other test spaces, and the invention is not limited in this regard. Moreover, the temperature and humidity sensing device 100 can also be configured to sense the temperature in a diaper, the temperature of other objects worn on the human body, or the temperature of other test spaces.

The temperature and humidity sensing device 100 includes a body 110 and a temperature and humidity sensor 120, wherein the body 110 adopts a double opening design, and the temperature and humidity sensor 120 is disposed in the body 110. The body 110 has an inlet hole 111, an outlet hole 112, and a flow channel 113, wherein the inlet hole 111 and the outlet hole 112 are opposite to each other, and the flow channel 113 is configured to communicate the inlet hole 111 and the outlet hole 112. The temperature and humidity sensor 120 is disposed in the flow channel 113 and is disposed in correspondence to the inlet hole 111. Therefore, air A in the surrounding environment of the body 110 can flow into the flow channel 113 from the inlet hole 111 and flow through the flow channel 113 to flow out from the outlet hole 112. As a result, the air A maintains a unidirectional flow in the flow channel 113, such that the humidity state in the flow channel 113 is close to the humidity state of the surrounding environment of the body 110. Accordingly, during the air A in the surrounding environment of the body flows into the flow channel 113 from the inlet hole 111 and flows through the flow channel 113 to flow out from the outlet hole 112, the temperature and humidity sensor 120 can rapidly and accurately sense the relative humidity of the air A in the surrounding environment of the body 110 and the temperature of the surrounding environment of the body 110.

Referring to FIG. 2 to FIG. 4, in the present embodiment, the body 110 includes a first case 1101 and a second case 1102 connected to each other, the inlet hole 111 is disposed on the first case 1101, and the outlet hole 112 is disposed on the second case 1102. The inlet hole 111 and the outlet hole 112 are staggered to each other, that is to say, the orthographic projection of the outlet hole 112 on the first case 1101 is not overlapped with the inlet hole 111. Moreover, the first case 1101 and the second case 1102 assembled together can define a housing space configured to house the temperature and humidity sensor 120 or other devices such that the temperature and humidity sensor 120 or other devices disposed in the housing space are not directly exposed to the outside.

The inside of the first case 1101 has a groove 114 and a trench 115, wherein the groove 114 is communicated with the inlet hole 111 and the groove 114 is communicated with the trench 115. The temperature and humidity sensing device 100 further includes a diversion tube 130 disposed between the first case 1101 and the second case 1102. The diversion tube 130 is located in a portion of the outlet hole 112 and the trench 115 and configured to communicate the trench 115 and the outlet hole 112. Moreover, the diversion tube 130 aligned to the outlet hole 112 and the inlet hole 111 are staggered to each other, that is to say, the orthographic projection of the diversion tube 130 on the first case 1101 is not overlapped with the inlet hole 111. Moreover, the trench 115 is extended from the location of the groove 114 toward the location of the diversion tube 130.

Referring further to FIG. 2 to FIG. 4, the temperature and humidity sensing device 100 further includes a circuit board 140 disposed between the first case 1101 and the second case 1102 and located in the housing space. An end 141 of the circuit board 140 covers the groove 114. The temperature and humidity sensor 120 is disposed at a side of the end 141 covering the groove 114 and electrically connected to the circuit board 140, that is to say, the temperature and humidity sensor 120 is located in the groove 114. Moreover, the temperature and humidity sensing device 100 further includes a gasket 150, and the gasket 150 is disposed on the first case 1101 and located between the circuit board 140 and the first case 1101. The gasket 150 covers a portion of the trench 115, and the gasket 150 has a first opening 151 and a second opening 152 opposite to each other and can be 8-shaped structure.

In the present embodiment, the first opening 151 is aligned to the groove 114 and the second opening 152 is aligned to the diversion tube 130. In the first case 1101, a positioning column 116 is disposed in the surrounding of the groove 114, the end 141 of the circuit board 140 has a positioning hole 142 corresponding to the positioning column 116, and a positioning hole 153 corresponding to the positioning column 116 is disposed in the surrounding of the first opening 151 of the gasket 150. During the process of disposing the gasket 150 on the first case 1101 and disposing the circuit board 140 on the gasket 150, the locations of the gasket 150 and the circuit board 140 on the first case 1101 can be fixed and the relative positions of the gasket 150 and the circuit board 140 can be fixed by the positioning column 116, the positioning hole 153, and the positioning hole 142. The end 141 of the circuit board 140 covers the first opening 151, and the temperature and humidity sensor 140 passes through the first opening 151 and is disposed in the groove 114.

Moreover, the gasket 150 is located between the diversion tube 130 and the first case 1101 and the second opening 151 exposes a portion of the trench 115 such that the trench 115 and the diversion tube 130 located in the second opening 151 are communicated with each other. In the present embodiment, the diversion tube 130 can be fixed to the gasket 150 by an adhesive, and the gasket 150 can be formed by a flexible material to increase the adhesion between the first case 110 and the gasket 150, the adhesion between the circuit board 140 and the gasket 150, and the adhesion between the diversion tube 130 and the gasket 150 to prevent the air A flowing through the flow channel 113 from escaping.

The temperature and humidity sensing device 100 further includes a gasket 160, wherein the gasket 160 is disposed between the diversion tube 130 and the second case 1102 and the gasket 160 has an opening 161. The opening 161 is aligned to the outlet port 132 of the diversion tube 130 and the outlet hole 112 of the second case 1102 to communicate the diversion tube 130 and the outlet hole 112. For instance, two opposite ends of the gasket 160 can be respectively fixed to the second case 1102 and the diversion tube 130 by an adhesive, and the gasket 160 can be formed by a flexible material to increase the adhesion between the second case 1102 and the gasket 160 and the adhesion between the diversion tube 130 and the gasket 160 to prevent the air A flowing through the flow channel 113 from escaping.

The diversion tube 130 has an inlet port 131, an outlet port 132 opposite to the inlet port 131, and a conduit 133, wherein the inlet port 131 is communicated with the trench 115 via the second opening 152, the conduit 133 communicates the inlet port 131 and the outlet port 132, and the outlet port 132 is communicated with the outlet hole 112 via the opening 161. More specifically, the flow channel 113 of the present embodiment is mainly formed by the groove 114, the trench 115, and the conduit 133 communicated with one another. A diameter D1 of the conduit 133 can be constant, wherein the length of the conduit 133 is defined as L and the ratio of the length L and the diameter D1 is made to be less than or equal to 5 to increase the flow efficiency of the air A flowing through the flow channel 113 flowing toward the outlet port 132 from the inlet port 131.

Referring to FIG. 4, an aperture D2 of the inlet hole 111 of the present embodiment is smaller than the aperture of the second opening 152, and the aperture of the second opening 152 is equal to the diameter D1 of the conduit 133, the aperture of the opening 161, and the aperture D3 of the outlet hole 112 to ensure the air A flowing into the flow channel 113 from the inlet hole 111 can flow toward the outlet hole 112. For instance, the ratio of the aperture D3 and the aperture D2 is between 1.0 and 1.8.

In other embodiments, the aperture of the inlet hole is smaller than the aperture of the second opening, and the aperture of the second opening is equal to the caliber of the inlet port of the diversion tube. Moreover, the diameter of the conduit is increased from the inlet port toward the outlet port, that is to say, the caliber of the outlet port of the conduit is greater than the caliber of the inlet port thereof to ensure air flowing into the flow channel from the inlet hole can flow toward the outlet hole. Moreover, the aperture of the opening and the aperture of the outlet hole can be made to be the same as the caliber of the outlet port or be increased from the outlet port to the outlet hole.

Figure 5:
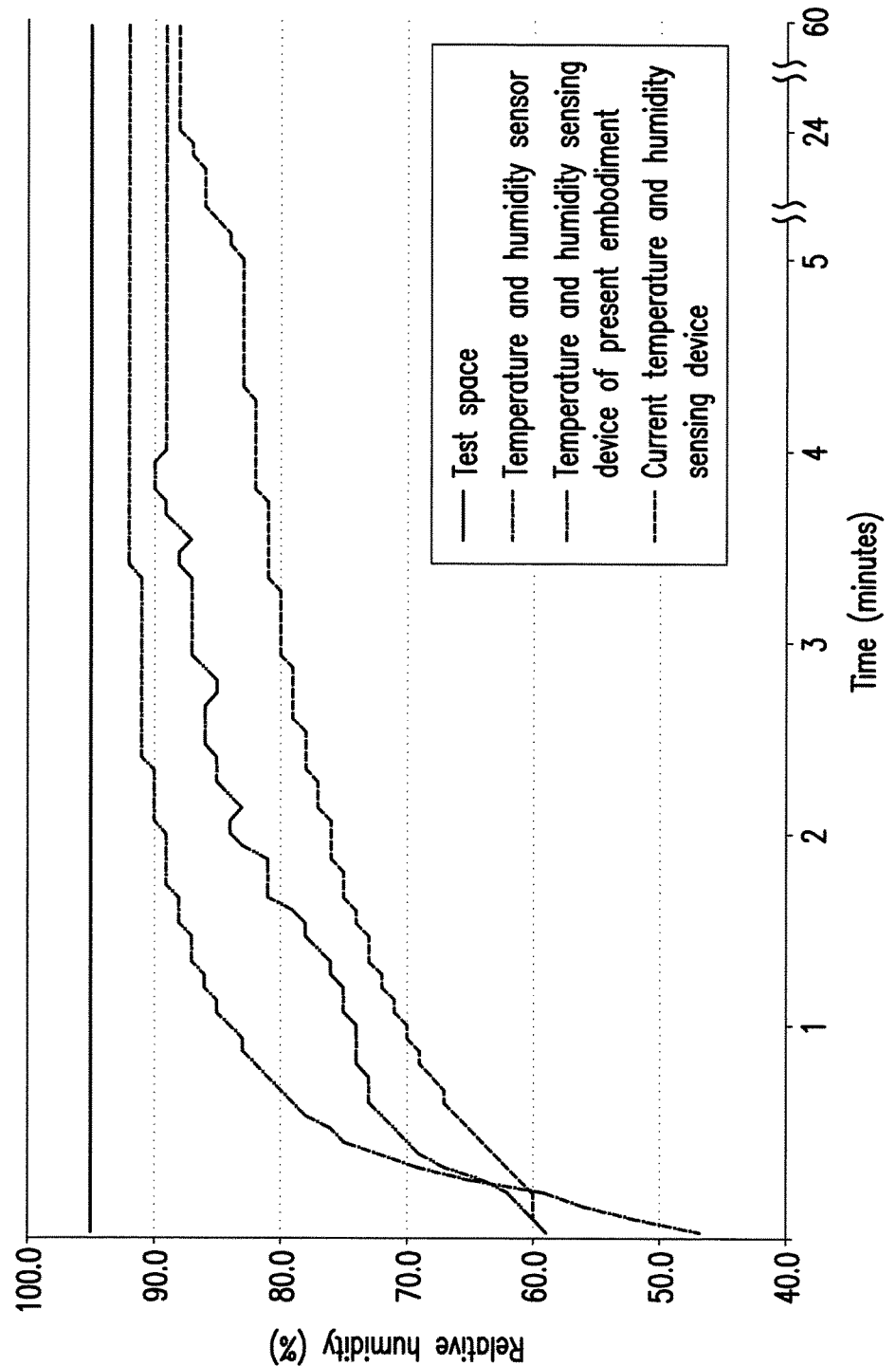
FIG. 5 is an experimental comparison chart of the temperature and humidity sensing device of FIG. 1.

FIG. 5 is an experimental comparison chart of the temperature and humidity sensing device of FIG. 1. FIG. 5 shows the relative humidity of a test space; the relative humidity obtained by disposing the temperature and humidity sensor in a test space and the corresponding sensing time thereof; the relative humidity obtained by disposing the temperature and humidity sensing device 100 of the present embodiment in a test space and the corresponding sensing time thereof; and the relative humidity obtained by disposing a current temperature and humidity sensing device (single opening design) in a test space and the corresponding sensing time thereof. In FIG. 5, the vertical axis represents relative humidity (%) and the horizontal axis represents sensing time (minutes).

Specifically, without the influence from temperature, pressure, or other external factors, the relative humidity of the test space is basically kept constant and does not change with time. In this case, the relative humidity of the test chamber is about 95% and is shown by a solid line in FIG. 5. The temperature and humidity sensor needs about 3 minutes and 30 seconds of sensing time to keep the resulting relative humidity at a constant value, and the resulting relative humidity in the test space is about 92% and is shown as a single dot-dash line in FIG. 5. The temperature and humidity sensing device 100 of the present embodiment needs about 4 minutes and 06 seconds of sensing time to keep the resulting relative humidity at a constant value, and the resulting relative humidity in the test space is about 89% and is shown as a double dot-dash line in FIG. 5. The current temperature and humidity sensing device (single opening design) needs about 24 minutes and 40 seconds of sensing tune to keep the resulting relative humidity at a constant value, and the resulting relative humidity in the test space is about 88% and is shown as a dashed line in FIG. 5.

It can be known from the experimental comparison that, the sensing time needed for the temperature and humidity sensing device 100 of the present embodiment is significantly less than the sensing time needed for the current temperature and humidity sensing device (single opening design), and the relative humidity obtained by the temperature and humidity sensing device 100 of the present embodiment is closer to the relative humidity of the test space than the current temperature and humidity sensing device (single opening design).

Based on the above, the temperature and humidity sensing device of the invention has an inlet hole and an outlet hole at two opposite sides of the body such that air in the surrounding environment of the body can flow into the flow channel from the inlet hole and flow through the flow channel to and flow out from the outlet hole. As a result, the air maintains a unidirectional flow in the flow channel, such that the humidity state in the flow channel is close to the humidity state of the surrounding environment of the body. Therefore, the sensing efficiency and the sensing accuracy of the temperature and humidity sensor disposed in the flow channel can be increased.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A temperature and humidity sensing device, comprising:
   a body, having an inlet hole, an outlet hole, and a flow channel, wherein the inlet hole and the outlet hole are opposite to each other, and the flow channel is configured to communicate the inlet hole and the outlet hole; and
   a temperature and humidity sensor, disposed in the flow channel, wherein the temperature and humidity sensor is configured to sense a relative humidity of air in a surrounding environment of the body during the air in the surrounding environment of the body flows into the flow channel from the inlet hole and flows through the flow channel to flow out from the outlet hole,
   wherein the body comprises a first case and a second case connected to each other, the inlet hole is disposed on the first case, and the outlet hole is disposed on the second case.

2. The temperature and humidity sensing device of claim 1, wherein an inside of the first case has a groove and a trench, the groove is communicated with the inlet hole, the groove is communicated with the trench, and the temperature and humidity sensor is located in the groove.

3. The temperature and humidity sensing device of claim 2, further comprising:
   a diversion tube, disposed between the first case and the second case, wherein the diversion tube is configured to communicate the trench and the outlet hole and the flow channel is formed by the groove, the trench, and the diversion tube.

4. The temperature and humidity sensing device of claim 3, further comprising:

a circuit board, disposed between the first case and the second case and covering the groove, wherein the temperature and humidity sensor is disposed at a side of the circuit board covering the groove and electrically connected to the circuit board.

5. The temperature and humidity sensing device of claim 4, further comprising:
a gasket, disposed on the first case and located between the circuit board and the first case, wherein the gasket covers a portion of the trench and has a first opening and a second opening disposed adjacent to each other, the first opening is aligned to the groove, the second opening is aligned to the diversion tube, the circuit board covers the first opening, and the temperature and humidity sensor passes through the first opening.

6. The temperature and humidity sensing device of claim 5, wherein the gasket is located between the diversion tube and the first case, and the second opening exposes a portion of the trench such that the trench and the diversion tube are communicated with each other.

7. The temperature and humidity sensing device of claim 3, wherein the diversion tube has an inlet port, an outlet port opposite to the inlet port, and a conduit, the inlet port is communicated with the trench, the conduit communicates the inlet port and the outlet port, and the outlet port is communicated with the outlet hole.

8. The temperature and humidity sensing device of claim 7, wherein a diameter of the conduit is constant.

9. The temperature and humidity sensing device of claim 7, wherein a diameter of the conduit is increased from the inlet port toward the outlet port.

10. The temperature and humidity sensing device of claim 3, further comprising:
a gasket, disposed between the diversion tube and the second case, wherein the gasket has an opening and is configured to communicate the diversion tube and the outlet hole.

* * * * *